US007379528B2

United States Patent
Mattson et al.

(10) Patent No.: US 7,379,528 B2
(45) Date of Patent: May 27, 2008

(54) RADIATION DETECTOR WITH SHIELDED ELECTRONICS FOR COMPUTED TOMOGRAPHY

(75) Inventors: Rodney A. Mattson, Mentor, OH (US); Randall P. Luhta, Highland Heights, OH (US); Marc A. Chappo, Elyria, OH (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 230 days.

(21) Appl. No.: 10/541,623

(22) PCT Filed: Dec. 17, 2003

(86) PCT No.: PCT/IB03/06268

§ 371 (c)(1),
(2), (4) Date: Jul. 6, 2005

(87) PCT Pub. No.: WO2004/061478

PCT Pub. Date: Jul. 22, 2004

(65) Prior Publication Data

US 2006/0165214 A1    Jul. 27, 2006

Related U.S. Application Data

(60) Provisional application No. 60/438,217, filed on Jan. 6, 2003.

(51) Int. Cl.
*H05G 1/60* (2006.01)
*H05G 1/64* (2006.01)
*G01T 1/24* (2006.01)

(52) U.S. Cl. .................. 378/19; 378/98.8; 250/370.09

(58) Field of Classification Search .................. 378/4, 378/19, 98.8, 189, 203; 250/370.09, 370.08, 250/370.11; 257/431, 437, 443, 436
See application file for complete search history.

(56) References Cited

U.S. PATENT DOCUMENTS 5,381,014 A * 1/1995 Jeromin et al. ........ 250/370.09
5,763,885 A * 6/1998 Murphy et al. ............ 250/352

(Continued)

FOREIGN PATENT DOCUMENTS

| GB | 2 365 379 A | 1/2002 |
|---|---|---|
| JP | 2002214352 | 7/2002 |
| WO | WO 01/84629 A2 | 11/2001 |
| WO | WO 01/84629 A3 | 11/2001 |

*Primary Examiner*—Irakli Kiknadze

(57) ABSTRACT

A radiation detector module includes a scintillator (62, 62', 162, 262) arranged to receive penetrating radiation of a computed tomography apparatus (10). The scintillator produces optical radiation responsive to the penetrating radiation. A detector array (66, 66', 166, 266) is arranged to convert the optical radiation into electric signals. Electronics (72, 72', 172, 272) are arranged on a side of the detector array opposite from the scintillator in a path of the penetrating radiation. A radiation shield (86, 86', 100, 100', 100", 186, 210, 210', 286, 286') is disposed between the detector array and the electronics to absorb the penetrating radiation that passes through the scintillator. The radiation shield includes openings (90, 90') that communicate between the detector array and the electronics. Electrical feedthroughs (88, 88', 102, 102', 102", 188, 212, 212', 288, 288') pass through the radiation shield openings and electrically connect the detector array and the electronics.

29 Claims, 16 Drawing Sheets

U.S. PATENT DOCUMENTS

| | | |
|---|---|---|
| 5,777,335 A | 7/1998 | Mochizuki et al. |
| 5,802,138 A | 9/1998 | Glasser et al. ............. 378/98.8 |
| 6,115,448 A * | 9/2000 | Hoffman ...................... 378/19 |
| 6,256,404 B1 * | 7/2001 | Gordon et al. .............. 382/131 |
| 6,393,092 B1 * | 5/2002 | Yoshida ....................... 378/19 |
| 6,707,066 B2 * | 3/2004 | Morishita .................... 257/59 |
| 6,838,673 B2 * | 1/2005 | Morishita ............. 250/370.09 |
| 2002/0070343 A1 | 6/2002 | Hoffman |

* cited by examiner

RADIATION DETECTOR WITH SHIELDED ELECTRONICS FOR COMPUTED TOMOGRAPHY

CROSS REFERENCE TO RELATED APPLICATIONS

This application claims the benefit of U.S. provisional application Ser. No. 60/438,217 filed Jan. 6, 2003, which is incorporated herein by reference.

The following relates to the radiation detection arts. It particularly relates to an x-ray detector array for computed tomography which employs back-contact photodiodes, and will be described with particular reference thereto. However, the following relates more generally to radiation detectors for various applications.

In computed tomography scanners, an x-ray source is mounted on a rotating gantry. An array of detectors is mounted on the rotating gantry opposite the source or on a stationary gantry surrounding the rotating gantry. Imaging radiation in the form of x-rays produced by the x-ray source pass through an examined object in an examination region and are detected by the detector array. In present computed tomography scanners, the detector array typically includes between four and sixty-four rows of detectors along the axial or Z-direction, and signal processing electronics are arranged at one or both sides of the detector array beyond the width of the x-ray beam.

As a total number of detector rows increases, it becomes increasingly difficult to interconnect remotely disposed processing electronics with the detector elements of the detector array. Hence, there is a need in the art for detector arrangements in which the electronics are more closely integrated with the detectors. In a suitable arrangement, the electronics are placed behind the detector array. However, in this arrangement the processing electronics are exposed to the imaging radiation. A scintillator of the radiation detector typically absorbs about 99% of incoming x-rays; however, the remaining about 1% of the radiation is sufficient to degrade the electronics over time. Moreover, the scintillator includes gaps in the crystal elements through which x-rays can pass at higher intensities.

To address radiation damage issues, use of radiation-hard processing electronics have been proposed. However, radiation-hard electronics are generally digital and only differentiate between binary signal levels. Analog ASICs typically used for processing computed tomography detector data are more sensitive to radiation damage than digital electronics. The radiation can cause gradual signal drift in the analog circuits due to radiation-induced charge build-up at transistor gates, as well as leakage currents in transistors that cause improper measurements and/or functional failures. Of course, the radiation can also cause a catastrophic failure of the ASIC. Radiation hardened ASICs also have several undesirable features. They are typically substantially larger than similar conventional ASICs, they are more expensive, and they can require more power per channel compared with conventional ASICs, which is significant in CT scanners with large numbers of detectors.

Another approach has been to block radiation exposure by coating the ASICs with a radiation-shielding material, such as a lead or tungsten layer. However, this complicates design since ASIC wiring loops around the electrically conductive shield to connect to unshielded edges, creating high densities of electrical conductors, potential capacitance problems between the closely spaced wires, and complex connections. Yet another approach has been to orient the electronics perpendicular to the detector array. Again, such an arrangement complicates detector design, and by itself does not fully shield the ASICs.

The present invention contemplates an improved apparatus and method that overcomes the aforementioned limitations and others.

According to one aspect, a radiation detector module is disclosed. A scintillator is arranged to receive penetrating radiation. The scintillator produces second radiation responsive to the penetrating radiation. A detector array is arranged to detect second radiation produced by the scintillator. Electronics are arranged on a side of the detector array opposite from the scintillator in a path to receive penetrating radiation that has passed through the scintillator. A radiation shield is disposed between the detector array and the electronics. The radiation shield is substantially absorbing with respect to the penetrating radiation. The radiation shield includes openings communicating between the detector array and the electronics. Electrical feedthroughs pass through the radiation shield openings and electrically connect the detector array and the electronics.

According to another aspect, a computed tomography scanner is disclosed, including a stationary gantry and a rotating gantry rotatably connected with the stationary gantry for rotation about an axis of rotation. An x-ray source is mounted to the rotating gantry for projecting a cone-beam of radiation through the axis of rotation. A tiled array of detector modules as set forth in the previous paragraph are disposed across the axis of rotation from the x-ray source. A reconstruction processor is provided for processing an output of the electronics into an image representation.

According to yet another aspect, a method is provided for detecting penetrating radiation traveling in a first direction. In a planar region having a front face transverse to the first direction, most of the penetrating radiation is converted into a second radiation. The second radiation and a remainder of the penetrating radiation is passed from a second face of the planar region. The second radiation is converted into electrical signals. The electrical signals are electrically communicated via feedthroughs in a radiation shield disposed behind the second face of the planar region to electronics disposed behind the radiation shield while the remainder of the penetrating radiation is absorbed with the radiation shield.

One advantage resides in facilitating arranging detector electronics in the path of the imaging radiation.

Another advantage resides in self-contained radiation detector modules that can be tiled to generate a large two-dimensional radiation detector for computed tomography imaging applications.

Yet another advantage resides in providing radiation shielding with substantial elimination of high detector array wiring densities through distribution of feedthroughs across an area of the radiation shield.

Numerous additional advantages and benefits will become apparent to those of ordinary skill in the art upon reading the following detailed description of the preferred embodiments.

The invention may take form in various components and arrangements of components, and in various process operations and arrangements of process operations. The drawings are only for the purpose of illustrating preferred embodiments and are not to be construed as limiting the invention.

Figure 1:
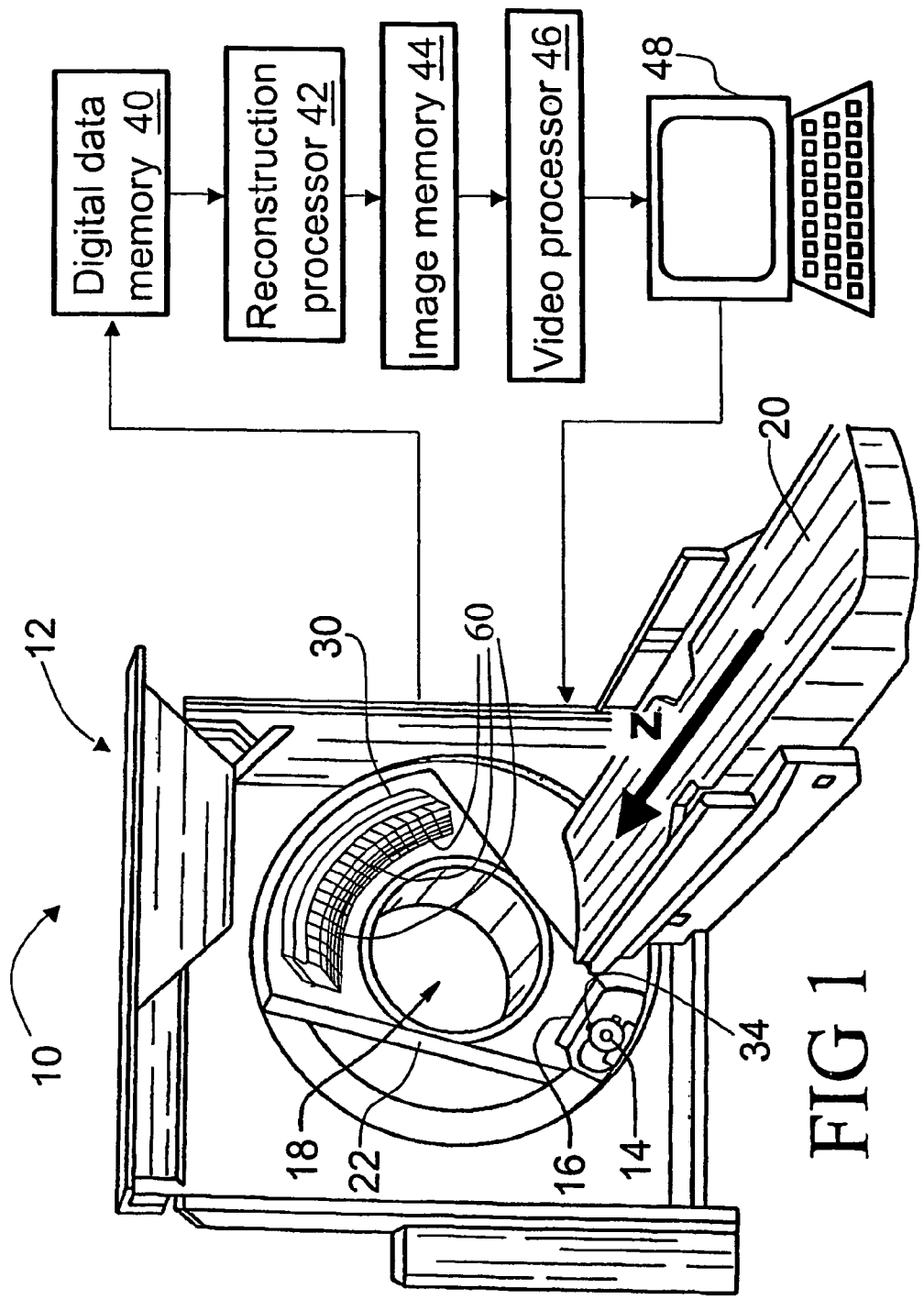
FIG. 1 shows an exemplary computed tomography imaging apparatus employing a radiation detector constructed in accordance with an embodiment of the invention.

With reference to FIG. 1, a computed tomography (CT) imaging apparatus or CT scanner 10 includes a stationary gantry 12. An x-ray source 14 and a source collimator shutter 16 cooperate to produce a fan-shaped, cone-shaped, wedge-shaped, or otherwise-shaped x-ray beam directed into an examination region 18 which receives a subject such as a patient arranged on a subject support 20. The subject support 20 is linearly movable in a Z-direction while the x-ray source 14 on a rotating gantry 22 rotates around the Z-axis.

The x-ray source 14 provides imaging radiation that passes through and is partially absorbed by the subject. In helical imaging, the rotating gantry 22 rotates simultaneously with linear advancement of the subject support 20 to produce a generally helical trajectory of the x-ray source 14 and collimator 16 about the examination region 18. In single- or multi-slice imaging, the rotating gantry 22 rotates as the subject support 20 remains stationary to produce a generally circular trajectory of the x-ray source 14 over which imaging data for an axial image is acquired. Subsequently, the subject support optionally steps a pre-determined distance in the Z-direction and the axial image acquisition is repeated to acquire volumetric data in discrete steps along the Z-direction.

A two-dimensional radiation detector 30 is arranged on the rotating gantry 22 across from the x-ray source 14 to detect the imaging radiation after passing through the subject. In the exemplary CT scanner 12, the radiation detector 30 spans a plurality of rows along the Z-direction, for example between four rows and sixty-four rows, with hundreds of detectors in each row. However, larger detector areas are contemplated.

The radiation detector 30 is constructed of tiled radiation detector modules each of which is a self-contained unit including a two-dimensional sub-array of detectors and electronics for driving the detectors and processing the detector signals. The radiation detector 30 is arranged on the rotating gantry 22 opposite to the x-ray source 14 and rotates therewith so that the radiation detector 30 receives x-rays that traverse the examination region 14 as the gantry 22 rotates.

Instead of the arrangement shown in FIG. 1, it is also contemplated to arrange the radiation detector on the stationary gantry 12 encircling the rotating gantry such that the x-rays impinge upon a continuously shifting portion of the radiation detector during source rotation.

With continuing reference to FIG. 1, the gantry 22 and the subject support 20 cooperate to obtain selected projection views of the subject along a helical trajectory or other trajectory of the x-ray source,14 relative to the subject. Projection data collected by the radiation detector 30 are communicated to a digital data memory 40 for storage.

A reconstruction processor 42 reconstructs the acquired projection data, using filtered backprojection, an n-PI reconstruction method, or other reconstruction method, to generate a three-dimensional image representation of the subject or of a selected portion thereof which is stored in an image memory 44. The image representation is rendered or otherwise manipulated by a video processor 46 to produce a human-viewable image such as that which is displayed on a display of a computer 48, or is printed by a printing device, or the like, for examination by a radiologist or other operator.

Preferably, the computer 48 is programmed to interface the radiologist or other operator with the CT scanner 12 to allow the radiologist to initialize, modify, execute, and control CT imaging sessions. The computer 48 is optionally interfaced with a communication network such as a hospital or clinic information network via which operations such as image reconstruction transmissions, a patient information recall, or the like are performed.

Figure 2:
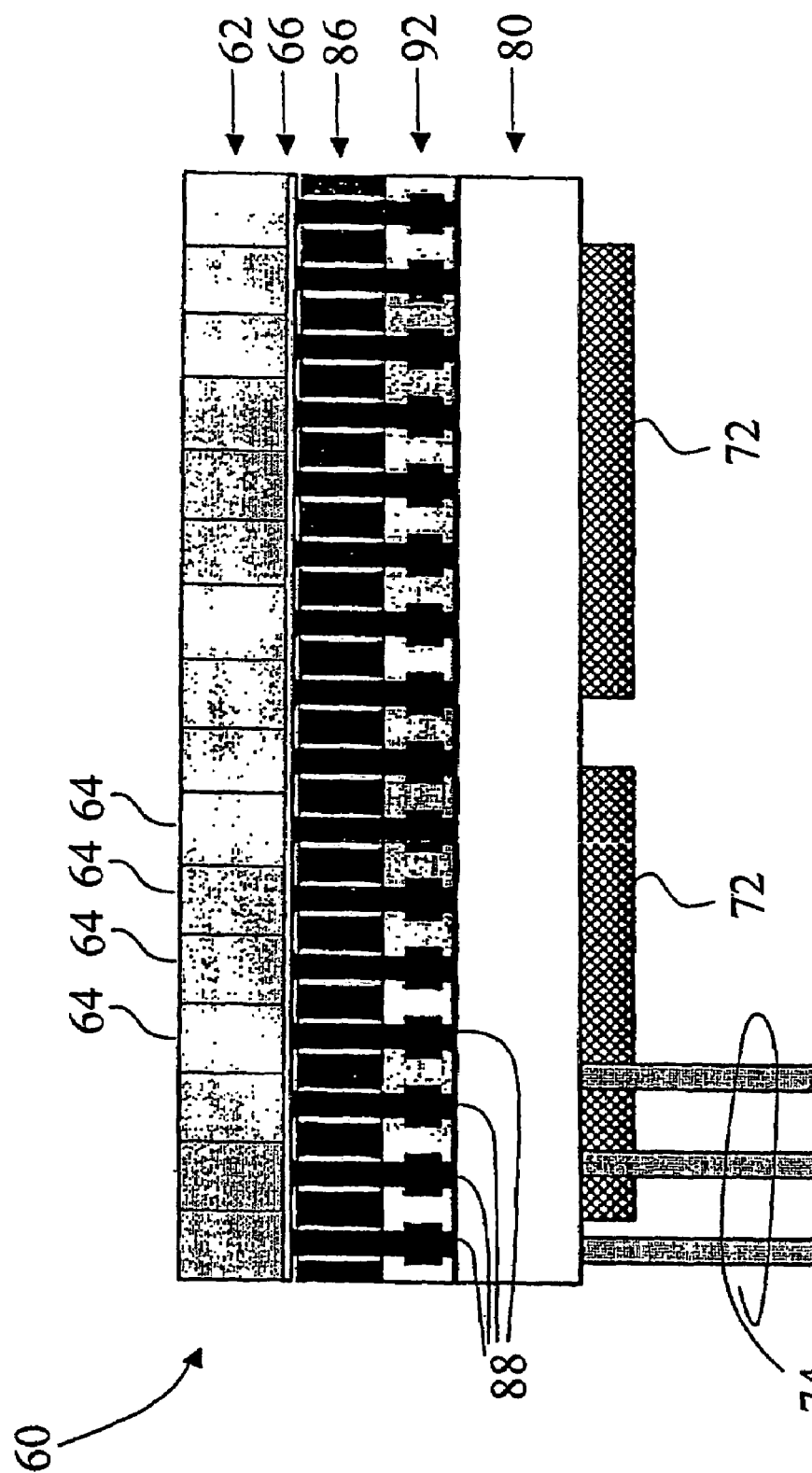
FIG. 2 shows a cross-sectional view of a radiation detector module with a radiation shield, and feedthroughs that are mounted on a rigid insulating mount and pass through the radiation shield.
Figure 3:
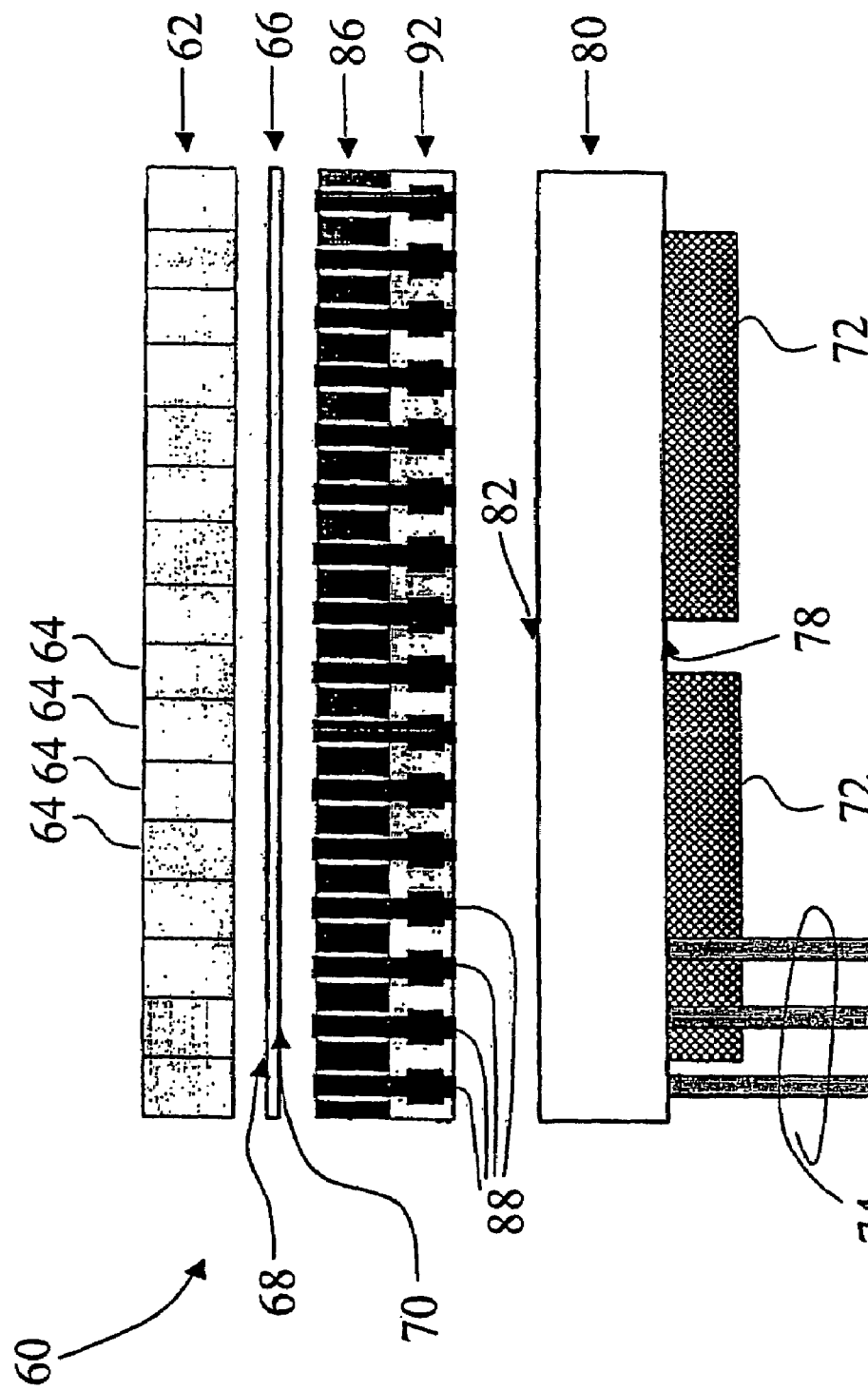
FIG. 3 shows an exploded cross-sectional view of the radiation detector module of FIG. 2.

With continuing reference to FIG. 1 and with further reference to FIGS. 2 and 3, the radiation detector 30 is formed of a plurality of radiation detector modules, such as a radiation detector module 60 shown in FIGS. 2 and 3. The radiation detector module 60 includes a scintillator 62 formed of an array of scintillator crystals 64. The scintillator 62 converts x-rays or other imaging radiation into second radiation, which is typically light in the visible, near infrared, or near-ultraviolet spectral range.

A photodetector array 66 is arranged to receive and detect the second radiation produced by the scintillator 62. Based upon detector signal intensities produced by the various detectors of the photodetector array 66, a scintillation event can be identified respective to particle energy (that is, photon energy for an x-ray photon) and lateral location on the detector array 66. The detectors of the array 66 are preferably back-contact photodiodes which, when arranged in the detector array 66, have a front side 68 that is sensitive to the second radiation produced by scintillation events, and also have a back side 70 on which electrical contacts are disposed. Back-contact photodiodes advantageously can be closely packed to form spatially dense detector array. Other detectors which convert light energy into electrical signals, such as front surface photodiodes with conductive thru holes to back surface contacts, and charge-coupled devices (CCDs), are also contemplated. Moreover, the scintillator/photodetector arrangement can be replaced by direct conversion detectors such as CZT detectors bump-bonded to a shielded substrate and associated behind the detector electronics.

Electronics, such as an exemplary two application-specific integrated circuits (ASICs) 72, produce electrical driving outputs for operating the detector array 66, and receive detector signals produced by the detector array 66. The ASICs 72 perform selected detector signal processing which results in the conversion of photodiode currents to digital data. The ASICs 72 produce output signals of the radiation detector module 60 which are transmitted through input/output (I/O) pins 74. Optionally, input signals are also communicated to the ASICs 72 via the I/O pins 74, for example to select a detector array biasing level.

The ASICs 72 are arranged on a back side 78 of a printed circuit board or ceramic substrate 80. Preferably, the printed circuit board or ceramic substrate 80 includes electrical paths that connect the ASICs 72 on the back side 78 with electrical contacts on a front side 82 of the printed circuit board or ceramic substrate 80.

Figure 4:
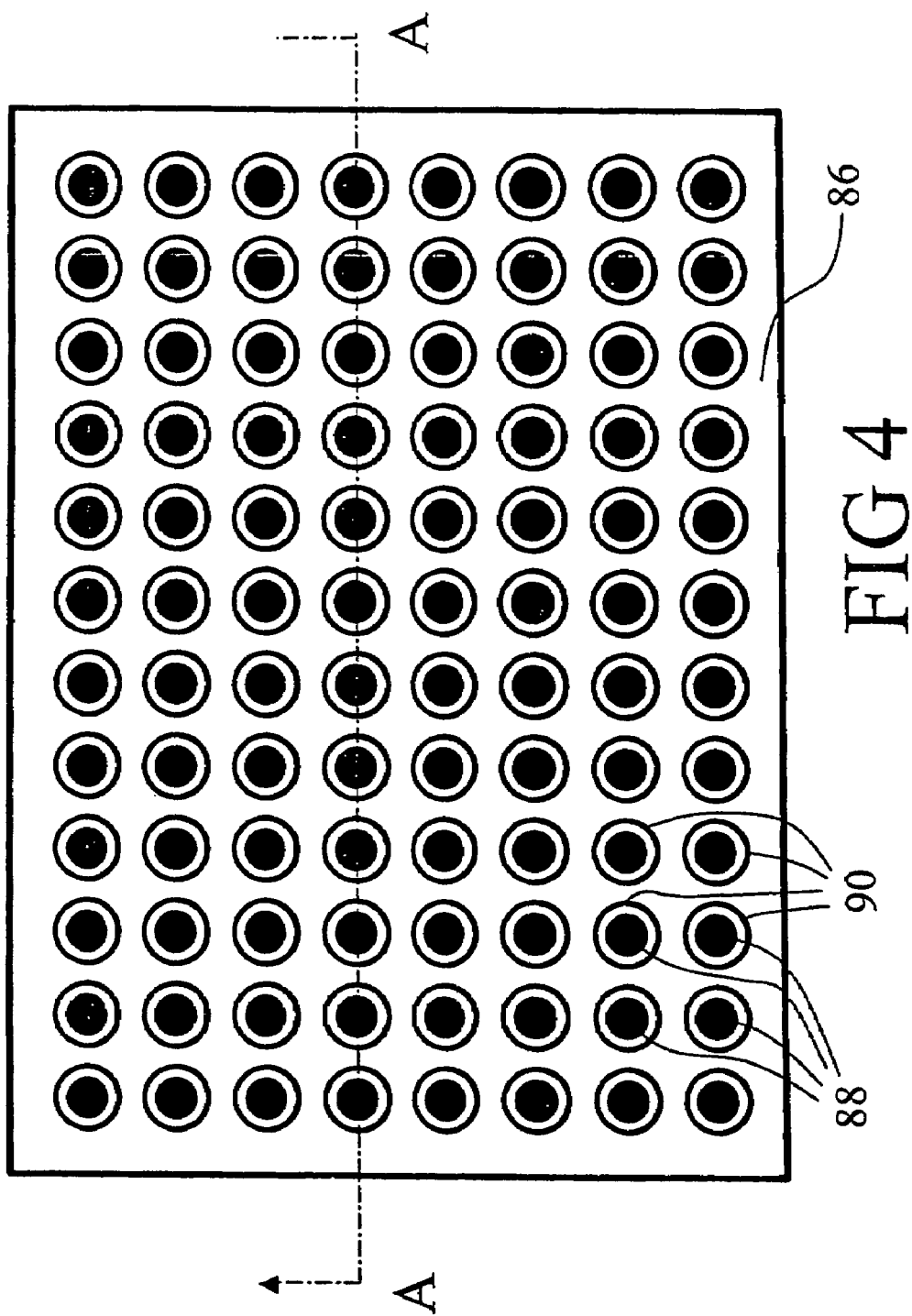
FIG. 4 shows a top view of the radiation shield and feedthroughs of the radiation detector module of FIG. 3.
Figure 5:
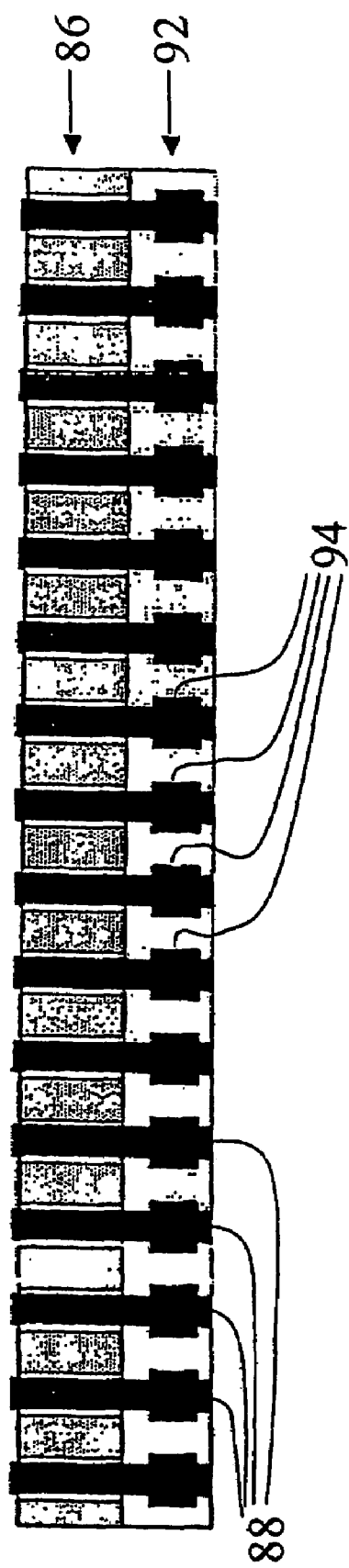
FIG. 5 shows cross-section A-A indicated in FIG. 4.

With continuing reference to FIGS. 1-3 and with further reference to FIGS. 4 and 5, a radiation shield 86 is disposed between the detector array 66 and the electronics 72, and more specifically in the embodiment of FIGS. 2-5 between the detector array 66 and the front side 82 of the printed circuit board or ceramic substrate 80. The radiation shield 86 includes a high-Z material, that is, a material with a substantial concentration of heavy atoms with high atomic number (Z). The atomic number Z corresponds to a total number of protons in the atom.

The high-Z material of the radiation shield 86 is dense in that it is highly absorbing for the imaging radiation, and the radiation shield 86 substantially absorbs impinging x-rays or other imaging radiation. Imaging radiation reaches the radiation shield 86 because about 1% of the incident imaging radiation passes through the scintillator crystals 64 of the scintillator 62. Additionally, imaging radiation can stream through gaps between the scintillator crystals 64 at substantially higher intensities. This passing radiation is absorbed by the radiation shield 86 or by high-Z feedthroughs 88 that are arranged in openings 90 (best seen in FIG. 4) of the radiation shield 86.

In the embodiment of FIGS. 2-5, the high-Z feedthroughs 88 are electrical conductors which are affixed to an electrically insulating rigid mount 92 that holds the feedthroughs 88 in an arrangement comporting with an arrangement of the openings 90 of the radiation shield 86. The radiation shield 86 forms an insert that is disposed over the feedthroughs 88 and atop the rigid mount 92 as shown in FIGS. 2, 3, and 5.

The radiation shield 86 can be electrically conducting or electrically insulating. However, if the radiation shield 86 is electrically conducting, then the electrical conductors 88 should not contact the radiation shield 86. Preferably, in such a case an insulating material is applied to at least one of the conductors 88 and the openings 90 to insulate the conductors 88 from the radiation shield 86.

Moreover, to block imaging radiation from passing through gaps between the feedthroughs 88 and edges of the openings 90 of the radiation shield 86, each feedthrough 88 preferably includes a widened portion 94 (labeled in FIG. 5) that laterally overlaps the corresponding opening 90. The widened portion 94 absorbs radiation that passes through the gaps.

The radiation shield 86 and feedthroughs are preferably made of a conducting high-Z material such as tungsten, a conducting tungsten alloy, lead, a conducting lead alloy, tantalum, gold, platinum, or the like. The radiation shield 86 can also be made of an insulating high-Z material such as an insulating lead oxide, bismuth trioxide, or the like. The radiation shield 86 can also be made of a composite material including an insulating binder such as an organic binder, polymeric material, or unsaturated polymeric resin, that supports a matrix of high-Z material such as lead oxide, bismuth trioxide, or oxides or salts of other high-Z elements. A non-insulating binder such as a eutectic alloy of lead and tin with a melting point lower than that of tungsten can also be used. The high-Z matrix is preferably in the form of a finely ground powder that is substantially uniformly distributed in the binder. Powder metallurgy technology employing powders of tungsten or tungsten compounds can be used for fabrication.

The shield 86 can be made relatively thick, for example a 1-3 centimeter thick shield is suitable. The thickness for a specific embodiment is selected based upon the x-ray absorption properties of the shield and feedthrough materials, along with any thickness constraints imposed by the physical structure of the radiation detector 30, and cost considerations.

Figure 6:
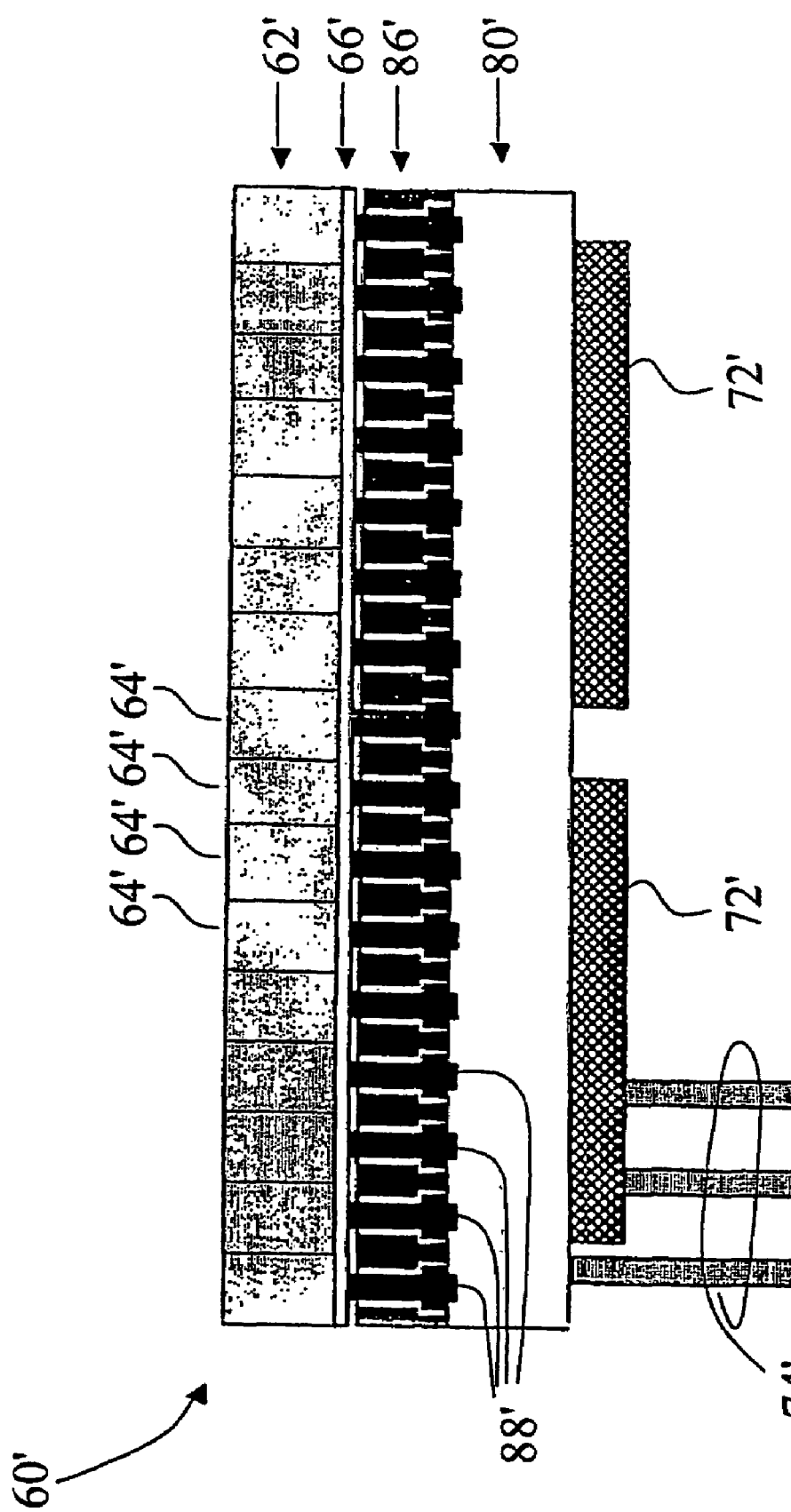
FIG. 6 shows a cross-sectional view of a radiation detector module that is similar to that of FIGS. 2-5. In the detector module of FIG. 6, the feedthroughs are secured to a printed circuit board or ceramic substrate that supports processing electronics.
Figure 7:
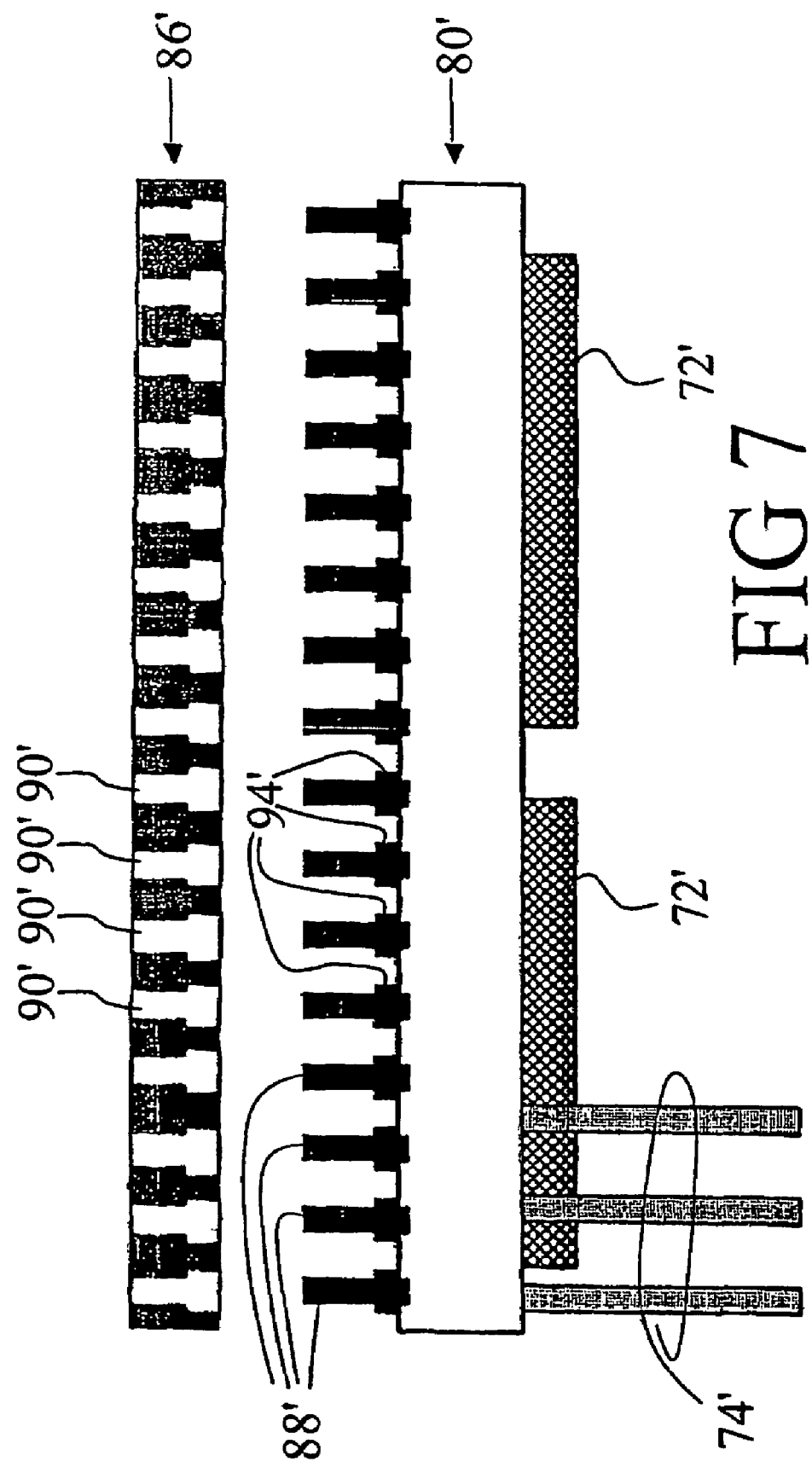
FIG. 7 shows the an exploded cross-sectional view of the radiation detector module of FIG. 6 with the scintillator and the detector array omitted.

FIGS. 6 and 7 show a radiation detector module 60' which is generally similar to the radiation detector module 60 of FIGS. 2-5. In FIGS. 6 and 7, components of the radiation detector module 60' that generally correspond to similar components of the radiation detector module 60 are labeled with corresponding primed numbers. The radiation detector module 60' includes a scintillator 62' with scintillator crystals 64', a detector array 66', a shield 86' with openings 90', ASICs 72', and 1/0 pins 74' that are generally similar to correspondingly labeled elements of the radiation detector module 60.

However, in the radiation detector module 60' the electrically insulating rigid mount 92 of the radiation detector module 60 is omitted. Feedthroughs 88' are instead directly anchored into a printed circuit board or ceramic substrate 80'. The feedthroughs 88' and the printed circuit board or ceramic substrate 80' are otherwise substantially similar to the corresponding components 88, 80 of the radiation detector module 60. Each feedthrough 88' includes a widened portion 94' that spatially overlaps a narrow portion of the corresponding radiation shield opening 90' to block imaging radiation from passing through gaps between the feedthrough 88' and the corresponding opening 90'.

Figure 8:
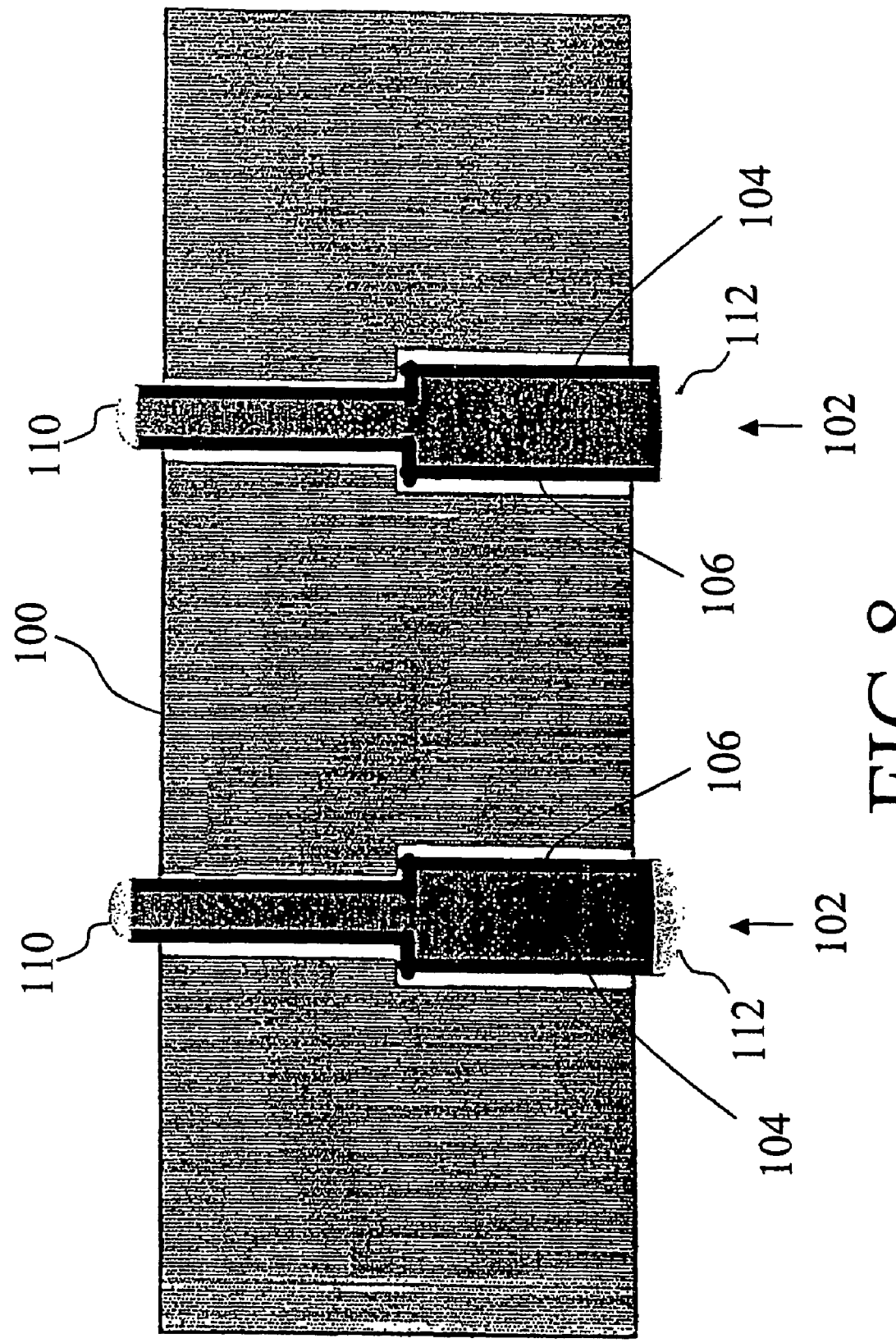
FIG. 8 shows a portion of a radiation shield in which insulated feedthroughs are press-fitted into openings of the radiation shield.

With reference to FIG. 8, another approach for constructing a radiation shield with cooperating high-Z feedthroughs is described. A radiation shield 100 (a portion of which is shown in cross-section in FIG. 8) has openings into which feedthroughs 102 are press-fitted. To avoid electrical contact with the radiation shield 100, the feedthroughs 102 include a conductive central conductor 104 coated with an insulating coating 106. A suitable insulating coating 106 is a Teflon coating.

To facilitate electrical contact with the detector array, a contact layer 110 (shown with exaggerated thickness) of gold or another highly conductive material is preferably electroplated, vacuum-deposited, or otherwise disposed on an end of the feedthrough 102 proximate to the detector array. Similarly, a contact layer 112 is preferably disposed on the other end of the feedthrough 102 for facilitating contact with electrical contact pads of the printed circuit board or ceramic substrate on which the electronics are disposed.

Figure 9:
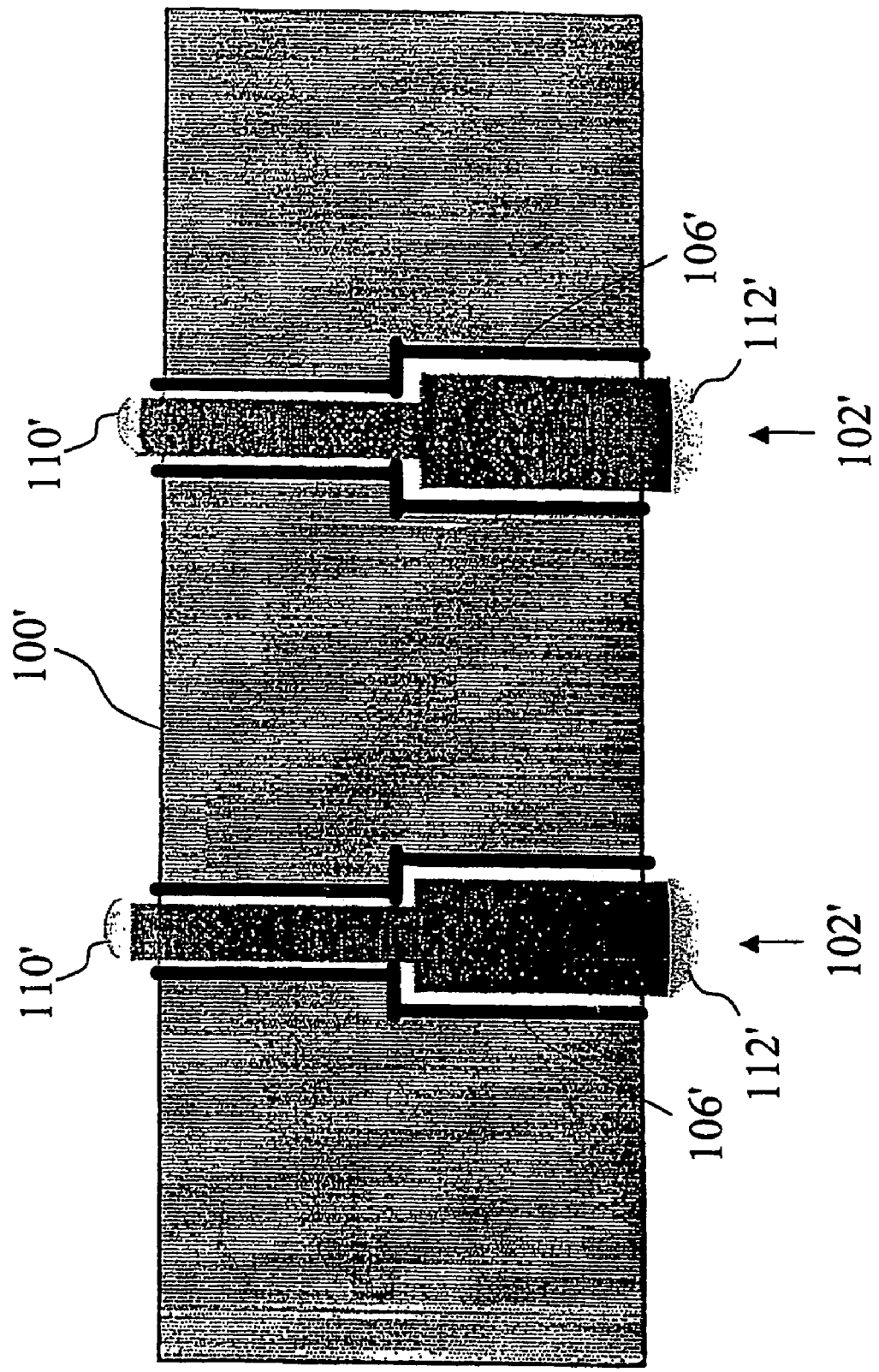
FIG. 9 shows a portion of a radiation shield in which feedthroughs are press-fitted into insulated openings of the radiation shield.

With reference to FIG. 9, in another press-fit embodiment, a radiation shield 100' (a portion of which is shown in cross-section in FIG. 9) has openings into which feedthroughs 102' are press-fitted. To avoid electrical contact with the radiation shield 100', the openings, rather than the feedthroughs, are coated with an insulating coating 106'. Preferably, contact layers 110', 112' are arranged on ends of the feedthroughs 102' for facilitating electrical communication with the detector array elements and with contact pads of the printed circuit board or ceramic substrate.

Figure 10:
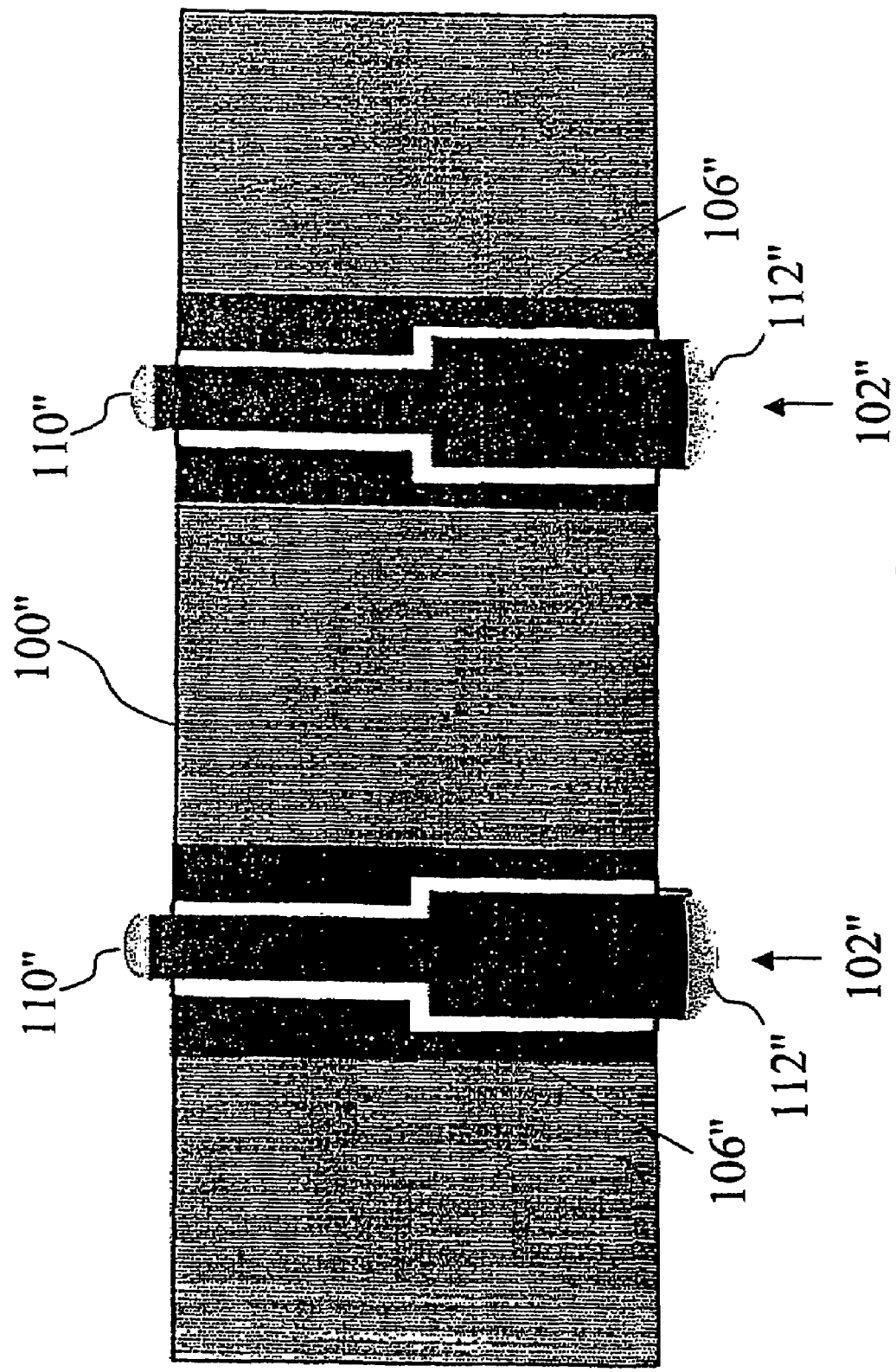
FIG. 10 shows a portion of a radiation shield in which feedthroughs are press-fitted into insulating inserts disposed in openings of the radiation shield.

With reference to FIG. 10, in yet another press-fit embodiment, a radiation shield 100" (a portion of which is shown in cross-section in FIG. 10) has openings into which feedthroughs 102" are press-fitted. To avoid electrical contact with the radiation shield 100", radiation-blocking insulative inserts 106" are arranged in the openings. The inserts 106" are suitably made of an insulating high-Z material such as an insulating lead oxide, bismuth trioxide, or the like. The inserts 106" can also be made of a composite material including an insulating binder such as an organic binder, polymeric material or unsaturated polymeric resin, and a matrix of high-Z material such as lead oxide, bismuth trioxide, or oxides or salts of other high-Z elements. Preferably, contact layers 110", 112" are arranged on ends of the feedthroughs 102" for facilitating electrical communication.

Figure 11:
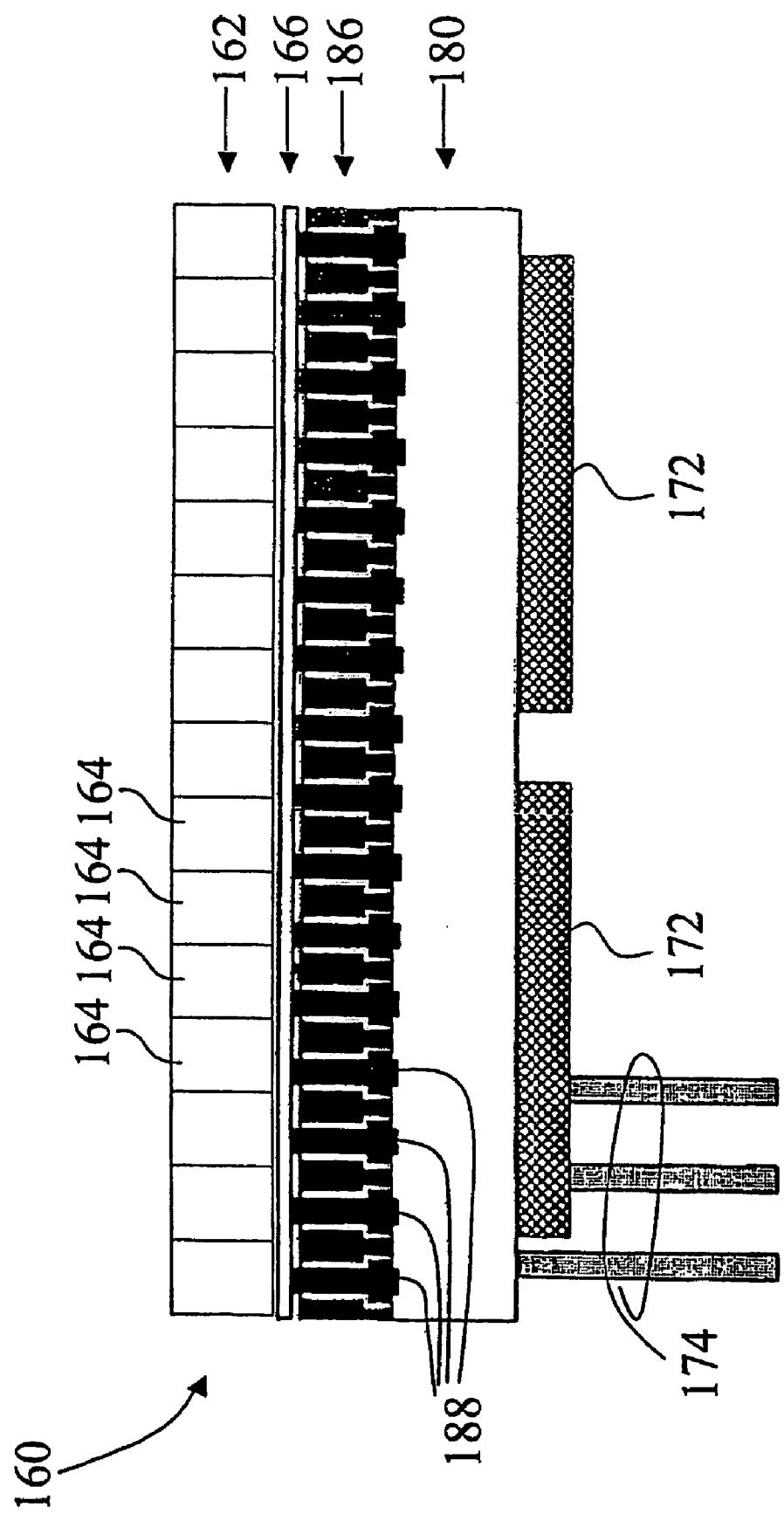
FIG. 11 shows a cross-sectional view of a radiation detector module that is similar to that of FIGS. 2-5. In the detector module of FIG. 11, insulated feedthroughs are embedded in a conductive radiation shield.
Figure 12:
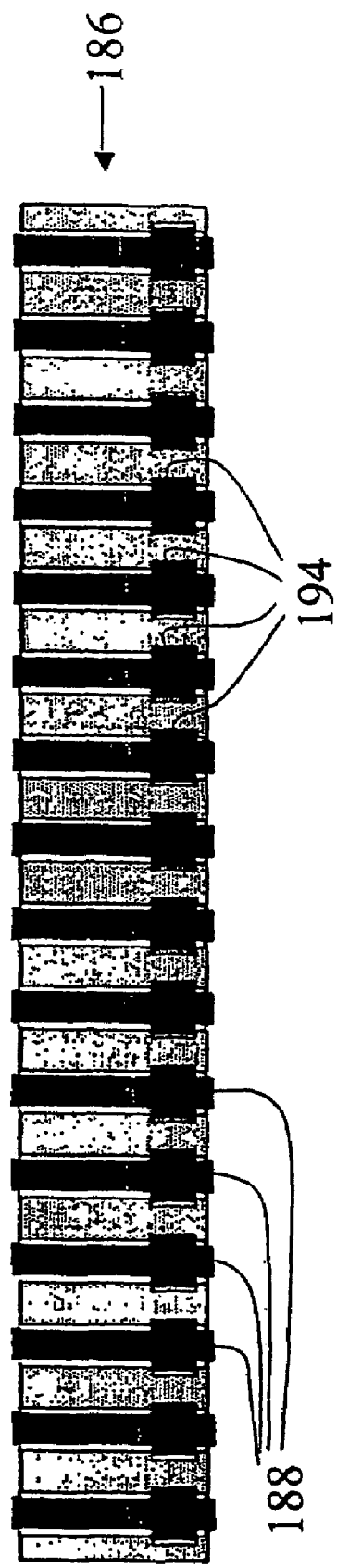
FIG. 12 shows a cross-sectional view of the radiation shield and embedded feedthroughs of the radiation detector module of FIG. 11.

With reference to FIGS. 11 and 12, a radiation detector module 160 is described, in which feedthroughs are embedded in the radiation shield. As with the radiation detector module 60, a scintillator 162 formed of scintillator crystals 164 converts the imaging radiation into second radiation. Typically, the scintillator 162 converts x-rays into visible, near-infrared, or near-ultraviolet light. A detector array 166, which is preferably an array of back-contact photodiodes, detects the second radiation and communicates detector signals to electronics 172, which are suitably embodied as one or more ASIC chips. I/O pins 174 transmit the detector signals after suitable processing by the electronics 172. The I/O pins 174 optionally also transmit control signals to the radiation detector module 160.

However, the radiation detector module 160 includes a radiation shield 186 that has feedthroughs 188 embedded in the radiation shield 186. The feedthroughs 188 are suitably metal conductors of a high-Z metal such as tungsten wires. The feedthroughs are suitably embedded by injection molding or casting of the radiation shield material to surround the feedthroughs 188.

If the radiation shield 186 is electrically conductive, then the feedthroughs 188 are preferably insulated with a Teflon or other insulating coating. Moreover, in such a case a widened feedthrough portion 194 is included to block imaging radiation from streaming through the feedthrough insulation.

Figure 13:
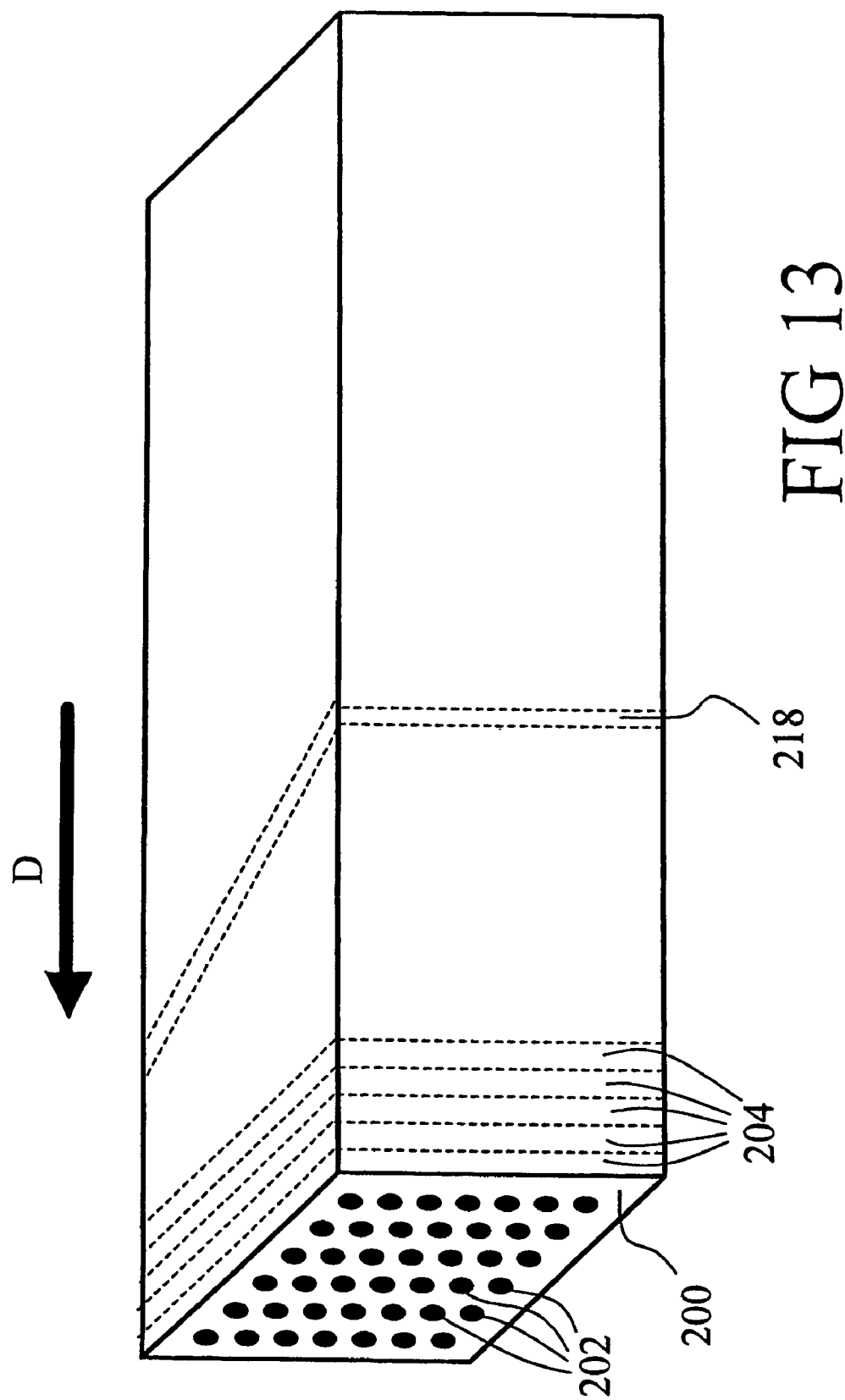
FIG. 13 shows an extrusion including an insulating radiation shield material co-extruded about electrical conductors. The extrusion is suitably sliced perpendicular to or at an angle to an extrusion direction to produce a radiation shield with embedded feedthroughs.

With reference to FIG. 13, in the case of an insulating radiation shield, the widened feedthrough portion is suitably omitted, and an insulating radiation shield with embedded feedthroughs is suitably fabricated by co-extrusion of a material 200 that forms the radiation shield onto tungsten wires 202 that form the feedthroughs. Instead of tungsten wires, gold wires can also be used.

Figure 14:
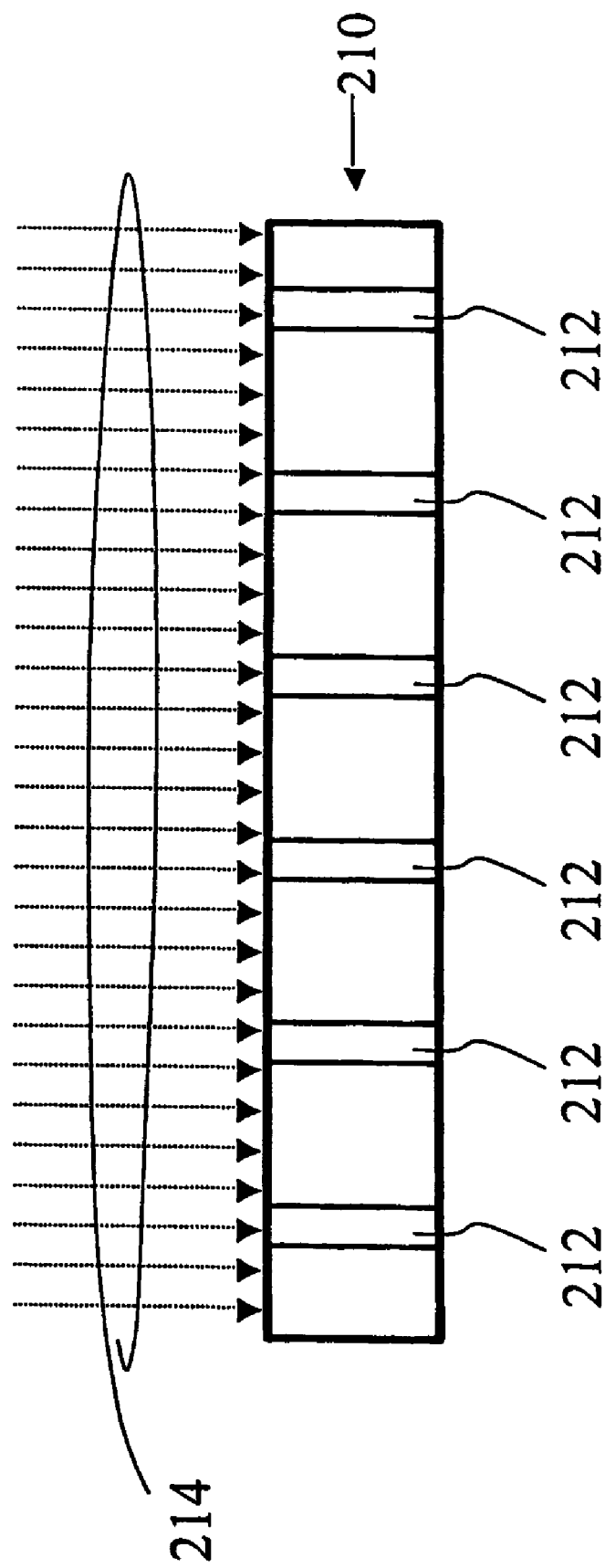
FIG. 14 shows a cross-sectional view of a radiation shield with embedded high-Z feedthroughs constructed from a perpendicular slice of the extrusion of FIG. 13.

With continuing reference to FIG. 13 and with further reference to FIG. 14, the extruding occurs through a rectangular extrusion die to produce a rectangular extrusion, and slices 204 taken perpendicular to an extruding direction D each form a rectangular radiation shield 210 (see FIG. 14) with tungsten feedthroughs 212 embedded therein. The radiation shield 210 and the feedthroughs 212 are each made of an image radiation-blocking high-Z material. For example, the feedthroughs 212 are suitably tungsten wires, while the radiation shield 210 is suitably a composite material including a powder of a high-Z material suspended in an extruded organic, polymeric, or unsaturated polymeric binder. Moreover, the embedded feedthroughs 212 are embedded in the radiation shield 210 with no gaps therebetween, and so imaging radiation 214 is fully blocked without widened feedthrough portions.

Figure 15:
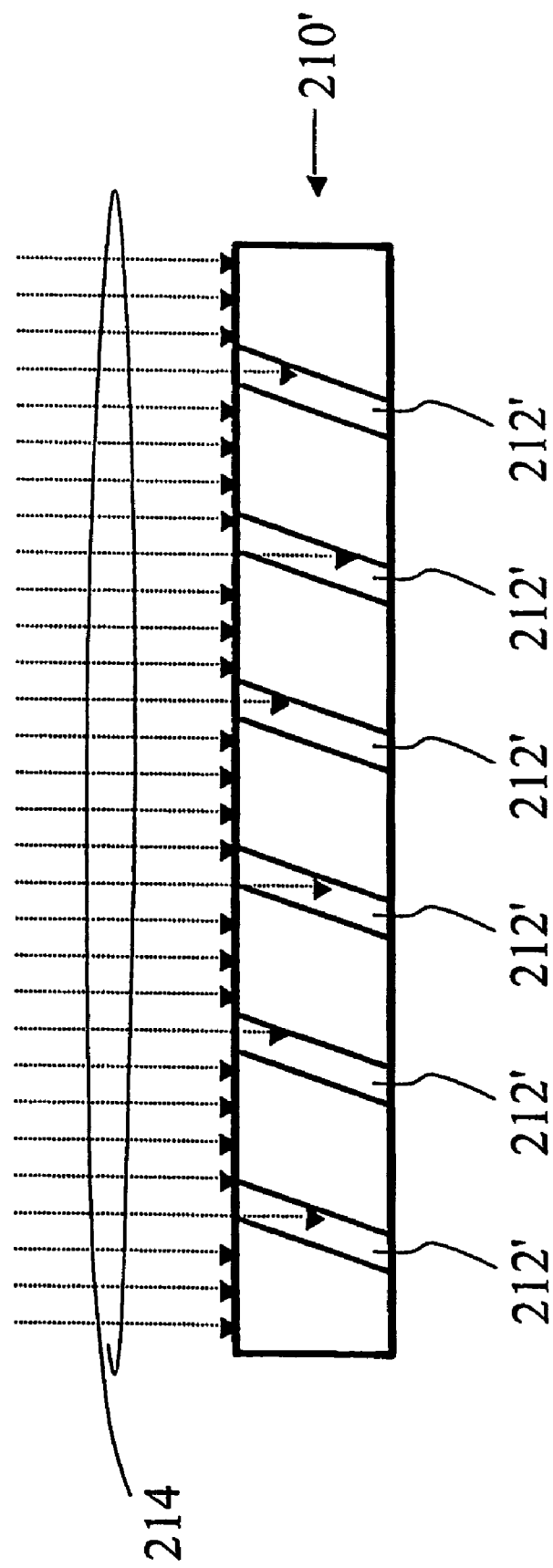
FIG. 15 shows a cross-sectional view of a radiation shield with embedded slanted low-Z feedthroughs constructed from slanted slice of the extrusion of FIG. 13.

With continuing reference to FIG. 13 and with further reference to FIG. 15, in an alternative extruded embedded feedthrough approach, insulating material 200 is extruded over wires 202 which in this embodiment are optionally not made of a high-Z material. That is, for the embodiment of FIG. 15 the wires 202 can be ordinary low-Z copper wires or other wires selected for high electrical conductivity, good contact resistance respective to the detector array and electronics contacts, and chemical, thermal, and like compatibility respective to the extruded insulating material 200. Moreover, rather than taking the perpendicular slices 204, a slanted slice 218 is taken, resulting in the shield 210' of FIG. 15.

Because of the slant of the slanted slice 218, the radiation shield 210' includes slanted feedthroughs 212'. The feedthroughs 212' are made of a low-Z material which is substantially non-absorbing for the imaging radiation 214. However, a computed tomography scanner produces highly collimated imaging radiation 214 on the scale of the radiation detector module. Hence, the imaging radiation 214 does not have a line-of-sight passage through the feedthroughs 212'. Rather than passing through the feedthroughs 212', imaging radiation is absorbed by the high-Z radiation shield 210' at the slanted walls.

Figure 16:
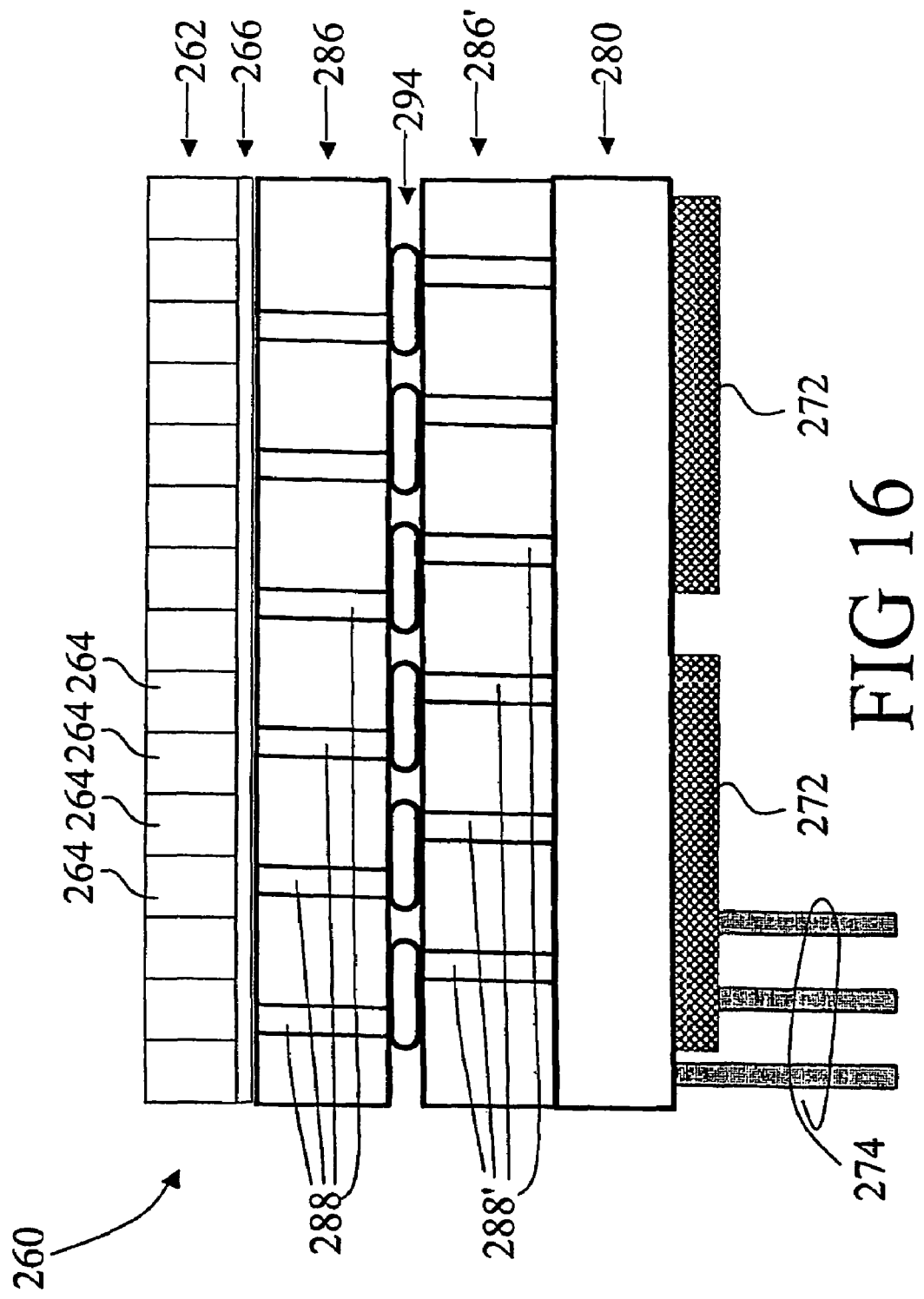
FIG. 16 shows a cross-sectional view of a radiation detector module that is similar to that of FIGS. 2-5. In the detector module of FIG. 16, the radiation shield includes two shield portions with laterally offset low-Z feedthroughs.

With reference to FIG. 16, another radiation detector module 260 that uses low-Z feedthroughs and a radiation shield geometry that prevents line-of-sight passage of imaging radiation therethrough is described. As with the radiation detector module 60, a scintillator 262 formed of scintillator crystals 264 converts the imaging radiation into second radiation. A detector array 266 detects the second radiation, and electronics 272 receive the detector signals. I/O pins 274 transmit the detector signals after suitable processing by the electronics 272. The I/O pins 274 optionally also transmit control signals to the radiation detector module 260. Moreover, as with the embodiment 60, the electronics 272 and the I/O pins 274 are disposed on a printed circuit board or ceramic substrate 280.

However, the radiation detector module 260 includes a radiation shield including two radiation shield portions 286, 286', each of which include feedthroughs 288, 288', respectively. The feedthroughs 288,288' are suitably copper wires or other low-Z metal conductors which do not provide substantial blocking of the imaging radiation. The radiation shield portions 286, 286' are electrically conductive or non-conductive. If conductive, then the feedthroughs 288, 288' are preferably insulated.

Rather than using imaging radiation-blocking feedthroughs, the radiation detector module 260 arranges the feedthroughs 288, 288' with a lateral offset in the radiation shield portions 286, 286' so that there is no line-of-sight via the feedthroughs 286, 286' between the imaging radiation source (e.g., the x-ray tube 14 of FIG. 1) and the electronics 272. To maintain electrical continuity, solder bumps 294 to provide electrical communication between the feedthroughs 286, 286'.

The radiation shields 286, 286' can be manufactured from perpendicular slices 204 of the extrusion of FIG. 13. Since the feedthroughs 288, 288' can be low-Z materials, the wires 202 of the extrusion are suitably low-Z wires. The radiation shields 286, 286' can also be manufactured by casting or injection molding.

In FIG. 16, the radiation shield portions 286, 286' are shown as separate elements from the printed circuit board or ceramic substrate 280. However, it is also contemplated to use the printed circuit board or ceramic substrate 280 as the offset radiation shield portion 286'. That is, the components 280, 286' can be replaced by a single unitary component which provides electronics interconnections, radiation shielding, and laterally offset feedthrough portions (respective to the feedthrough portions 288).

In constructing one of the above-described radiation shields 86, 86', 100,100', 100", 186, 210, 210', 286, 286' or their equivalents, several factors should be considered. Thermal expansion coefficients of the materials should be matched to avoid mechanical stresses as the radiation detector 30 heats up. Advantageously, several tungsten alloys have similar thermal expansion coefficients to that of silicon, and so a tungsten alloy radiation shield substantially thermally matches a silicon-based back-contact photodiode array.

To efficiently perform electrical contacting, conductive epoxy bump-bonding is a preferred approach for electrically connecting the detector array and the feedthroughs of the radiation shield, and for electrically connecting the feedthroughs and contact pads of the printed circuit board or ceramic substrate. Alternatively, solder bump-bonding can be used. To simplify the bump-bonding and increase reliability of the manufactured radiation detector module, the feedthrough ends on each side of the radiation shield should be planar to within about 0.01 centimeters or less. The feedthrough ends can be planarized by mechanical grinding or polishing, or by using suitable fixtures and processes during construction of the radiation shield and feedthroughs.

The described radiation detector modules are preferably tiled to define a complete detector array of the radiation detector 30. Presently, 2.5×2.5 cm$^2$ to 2.5×12 cm$^2$ radiation detector modules are preferred, corresponding to detector arrays of 16×32 detectors to 16×512 detectors. However, larger radiation detector modules can be constructed, and the optimal module area will depend upon the selected radiation shield, material constraints, and other factors. Each radiation detector module can be fully self-contained, since the signal processing electronics are shielded from the imaging radiation.

For radiation shields constructed of composite materials that include a high-Z matrix suspended in a binding material, suitable tradeoffs can be made between the radiation shield thickness and the concentration of high-Z matrix powder in suspension to obtain a desired level of radiation blocking. Moreover, if the binder is an insulating material while the matrix is a tungsten or other conductive powder, electrical conductivity of the radiation shield can be controlled based on the suspended high-Z matrix powder concentration.

For radiation shields 100, 100', 100" that employ press-fitted feedthroughs 102, 102', 102" (see FIGS. 8-10) the feedthroughs can have substantially any tapered shape. For example, feedthroughs having a shape corresponding to a frustum of a cone are suitable.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

The invention claimed is:

1. A radiation detector module including:
   a scintillator arranged to receive penetrating radiation, the scintillator producing second radiation responsive to the penetrating radiation;
   a detector array arranged to detect second radiation produced by the scintillator;
   electronics arranged on a side of the detector array opposite from the scintillator in a path to receive penetrating radiation that has passed through the scintillator;
   a radiation shield disposed between the detector array and the electronics, the radiation shield being substantially absorbing with respect to the penetrating radiation, the radiation shield including openings communicating between the detector array and the electronics;
   electrical feedthroughs passing through the radiation shield openings and electrically connecting the detector array and the electronics; and
   an insulating support that retains the electrical feedthroughs in an arrangement comporting with an arrangement of the radiation shield openings.

2. The radiation detector module as set forth in claim 1, wherein detector array includes:
   back-contact photodetectors each having a second radiation-sensitive side facing the scintillator and an electrical contacting side facing the radiation shield.

3. The radiation detector module as set forth in claim 1, wherein the radiation shield is electrically insulating.

4. The radiation detector module as set forth in claim 1, wherein the radiation shield is electrically conductive and the electrical feedthroughs include:
   an electrical conductor; and
   an insulator electrically isolating the electrical conductor from the radiation shield.

5. The radiation detector module as set forth in claim 1, wherein the insulating support is pan of the radiation shield.

6. The radiation detector module as set forth in claim 1, wherein the electrical feedthroughs are substantially absorbing with respect to the penetrating radiation and cooperate with the radiation shield to shield the electronics from the penetrating radiation that has passed through the scintillator.

7. The radiation detector module as set forth in claim 6, wherein each electrical feedthrough includes:
   a widened portion that spatially overlaps a narrower portion of the corresponding radiation shield opening.

8. The radiation detector module as set forth in claim 1, wherein the radiation shield includes a high-Z material.

9. The radiation detector module as set forth in claim 8, wherein the high-Z material is selected from a group consisting of tungsten, a tungsten alloy, lead, a lead alloy, a lead oxide, bismuth trioxide, tantalum, gold, and platinum.

10. The radiation detector module as set forth in claim 1, wherein the radiation shield is formed of a composite material including an insulating binder and a matrix of high-Z material.

11. The radiation detector module as set forth in claim 10, wherein the insulating binder is selected from a group consisting of an organic binder, a polymeric material, and an unsaturated polymeric resin.

12. The radiation detector module as set forth in claim 1, wherein each electrical feedthrough includes:
a high-Z conductor formed of a high-Z material.

13. The radiation detector module as set forth in claim 12, wherein the high-Z material is selected from a group consisting of tungsten, lead, an alloy of tungsten, an alloy of lead, tantalum, gold, and platinum.

14. The radiation detector module as set forth in claim 12, wherein each electrical feedthrough further includes:
an insulating coating surrounding the high-Z conductor.

15. The radiation detector module as set forth in claim 12, wherein each electrical feedthrough further includes:
at least one contact layer disposed on an end of the feedthrough that electrically communicates between the feedthrough and at least one of the detector array and the electronics.

16. The radiation detector module as set forth in claim 15, wherein the contact layer includes a gold layer.

17. The radiation detector module as set forth in claim 1, wherein ends of the electrical feedthroughs generally align with a surface of the radiation shield to define a flat surface.

18. The radiation detector module as set forth in claim 1, wherein each radiation shield opening is slanted relative to an incoming direction of the penetrating radiation to prevent the penetrating radiation from passing through the opening.

19. The radiation detector module as set forth in claim 1, further including:
a second radiation shield disposed between the detector array and the electronics, the second radiation shield being substantially absorbing with respect to the penetrating radiation;
second electrical feedthroughs passing through openings of the second radiation shield, the second electrical feedthroughs being spatially offset respective to the first electrical feedthroughs that pass through openings of the first radiation shield to prevent penetrating radiation from reaching the electronics; and
electrical connectors connecting selected electrical feedthroughs and second electrical feedthroughs to electrically connect the detector array and the electronics.

20. A computed tomography scanner including:
a stationary gantry;
a rotating gantry rotatably connected with the stationary gantry for rotation about an axis of rotation;
an x-ray source mounted to the rotating gantry for projecting a cone-beam of radiation through the axis of rotation;
a tiled array of detector modules as set forth in claim 1 disposed across the axis of rotation from the x-ray source, wherein a radiation shield is disposed between the tiled array and electronics, and an isolated electrical conductor provides an electrical path between the tiled array and the electronics through an opening in the radiation shield; and
a reconstruction processor for processing an output of the electronics into an image representation.

21. The radiation detector module claim 1, wherein the radiation shield is disposed atop the insulating support in a direction of the radiation.

22. The radiation detector module of claim 21, wherein the insulating support is a single unitary structure.

23. The radiation detector module of claim 21, wherein the radiation shield forms an insert that is disposed over the feedthroughs.

24. A method for detecting penetrating radiation traveling in a first direction, the method comprising:
in a planar region having a front face transverse to the first direction, converting most of the penetrating radiation into a second radiation;
passing the second radiation and a remainder of the penetrating radiation from a second face of the planar region;
converting the second radiation into electrical signals;
electrically communicating the electrical signals via feedthroughs in a radiation shield disposed behind the second face of the planar region to electronics disposed behind the radiation shield while absorbing the remainder of the penetrating radiation with the radiation shield, wherein the electrical signals are communicated over electrical conductors electrically isolated from the radiation shield.

25. The method as set forth in claim 24, wherein the absorbing of the remainder of the penetrating radiation further includes:
absorbing penetrating radiation with the feedthroughs to prevent the penetrating radiation from reaching the electronics.

26. The method as set forth in claim 24, further including:
extruding the radiation shield with the feedthroughs embedded therein.

27. The method as set forth in claim 24, further including:
arranging the feedthroughs in the radiation shield such that the penetrating radiation is prevented from passing through the feedthroughs or between the feedthroughs and the shield.

28. A radiation detector module including:
a scintillator arranged to receive penetrating radiation, the scintillator producing second radiation responsive to the penetrating radiation;
a detector array arranged to detect second radiation produced by the scintillator;
electronics arranged on a side of the detector array opposite from the scintillator in a path of penetrating radiation traversing the scintillator;
a radiation shield disposed between the detector array and the electronics, the radiation shield being substantially absorbing with respect to the penetrating radiation traversing the scintillator, the radiation shield including openings communicating between the detector array and the electronics, wherein each radiation shield opening is slanted relative to an incoming direction of the penetrating radiation traversing the scintillator to prevent the penetrating radiation traversing the scintillator from passing through the opening; and
electrical feedthroughs passing through the radiation shield openings and electrically connecting the detector array and the electronics.

29. A radiation detector module including:
a scintillator that receives radiation, wherein the scintillator produces second radiation responsive to the received radiation;
a detector array that detects the second radiation;
electronics arranged on a side of the detector array opposite from the scintillator in a path radiation traversing the scintillator;
a first radiation shield disposed between the detector array and the electronics, wherein the first radiation shield substantially absorbs the radiation traversing the scintillator and includes openings between the detector array and the electronics;

first electrical feedthroughs passing through the first radiation shield openings and electrically connecting the detector array and the electronics;

a second radiation shield disposed between the detector array and the electronics, wherein the second radiation shield substantially absorbs the radiation traversing the scintillator;

second electrical feedthroughs passing through openings of the second radiation shield, wherein the second electrical feedthroughs are spatially offset from the first electrical feedthroughs to prevent radiation traversing the scintillator from reaching the electronics; and electrical connectors connecting selected first electrical feedthroughs and second electrical feedthroughs to electrically connect the detector array and the electronics.

* * * * *